US008406883B1

(12) United States Patent
Barker

(10) Patent No.: US 8,406,883 B1
(45) Date of Patent: Mar. 26, 2013

(54) LEAD ASSEMBLY FOR ELECTRICAL STIMULATION SYSTEMS AND METHODS OF MAKING AND USING

(75) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1238 days.

(21) Appl. No.: 11/965,627

(22) Filed: Dec. 27, 2007

(51) Int. Cl.
*A61N 1/372* (2006.01)

(52) U.S. Cl. .......................................... 607/37; 607/116

(58) Field of Classification Search ............... 607/37–38, 607/116; 439/909
See application file for complete search history.

(56) References Cited

U.S. PATENT DOCUMENTS

| | | | |
|---|---|---|---|
| 4,705,042 A | 11/1987 | Giurtino | |
| 5,082,453 A | 1/1992 | Stutz, Jr. | |
| 5,560,358 A | 10/1996 | Arnold et al. | |
| 5,730,628 A | 3/1998 | Hawkins | |
| 6,181,969 B1 | 1/2001 | Gord | |
| 6,415,168 B1 | 7/2002 | Putz | |
| 6,430,442 B1 | 8/2002 | Peters et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,671,534 B2 | 12/2003 | Putz | |
| 6,725,096 B2 | 4/2004 | Chinn et al. | |
| 6,741,892 B1 | 5/2004 | Meadows et al. | |
| 6,925,334 B1 | 8/2005 | Salys | |
| 7,175,478 B2 * | 2/2007 | Ollivier ......................... 439/669 | |
| 7,244,150 B1 | 7/2007 | Brase et al. | |
| 2002/0095079 A1 | 7/2002 | Putz | |
| 2002/0143376 A1 | 10/2002 | Chinn et al. | |
| 2004/0059392 A1 | 3/2004 | Parramon et al. | |
| 2004/0093051 A1 | 5/2004 | Chinn et al. | |
| 2005/0234522 A1 * | 10/2005 | Ley et al. ......................... 607/37 |
| 2006/0167522 A1 | 7/2006 | Malinowski | |
| 2007/0150007 A1 | 6/2007 | Anderson et al. | |
| 2007/0150036 A1 | 6/2007 | Anderson | |
| 2007/0161294 A1 * | 7/2007 | Brase et al. ................... 439/668 |
| 2007/0209595 A1 | 9/2007 | Umegard et al. | |

(Continued)

FOREIGN PATENT DOCUMENTS

| | | |
|---|---|---|
| WO | 03/061469 A1 | 7/2003 |
| WO | 2008/016881 A2 | 2/2008 |

OTHER PUBLICATIONS

U.S. Appl. No. 11/393,991, filed Mar. 30, 2006.

(Continued)

*Primary Examiner* — Joseph Stoklosa
(74) *Attorney, Agent, or Firm* — Frommer Lawrence & Haug LLP; Patrick R. Turner

(57) ABSTRACT

A multi-contact connector includes a connector body having a substantially-tubular shape with a longitudinal surface and a distal end. The connector body includes at least one lumen and defines at least one port. At least one of the lumens extends from the distal end of the connector body to at least one of the ports disposed on the longitudinal surface of the connector body. The multi-contact connector also includes a flexible-circuit sleeve with a substantially-tubular shape and an exterior surface. The flexible-circuit sleeve includes a plurality of contact terminals disposed on the exterior surface and at least one slot extending through the flexible-circuit sleeve to allow contact with at least one of the contact terminals from inside the flexible-circuit sleeve. The flexible-circuit sleeve is configured and arranged to be disposed over at least a portion of the connector body.

20 Claims, 11 Drawing Sheets

U.S. PATENT DOCUMENTS

2007/0239243 A1 10/2007 Moffitt et al.
2008/0027504 A1 1/2008 Bedenbaugh

OTHER PUBLICATIONS

U.S. Appl. No. 11/396,309, filed Mar. 31, 2006.
U.S. Appl. No. 11/238,240, filed Sep. 29, 2005 (19 pages).
U.S. Appl. No. 11/532,844, filed Sep. 18, 2006 (25 pages).
U.S. Appl. No. 11/609,586, filed Dec. 12, 2006 (22 pages).
U.S. Appl. No. 11/694,769, filed Mar. 30, 2007 (24 pages).
U.S. Appl. No. 11/773,867, filed Jul. 5, 2007 (23 pages).
U.S. Appl. No. 11/855,033, filed Sep. 13, 2007 (21 pages).

* cited by examiner

LEAD ASSEMBLY FOR ELECTRICAL STIMULATION SYSTEMS AND METHODS OF MAKING AND USING

FIELD

The present invention is directed to the area of implantable electrical stimulation systems and methods of making and using the systems. The present invention is also directed to implantable electrical stimulation systems that include a lead assembly with a multi-contact connector at a proximal end of the lead assembly, as well as methods of making and using the lead assemblies.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a multi-contact connector that includes a connector body having a substantially-tubular shape with a longitudinal surface and a distal end. The connector body includes at least one lumen and defines at least one port. At least one of the lumens extends from the distal end of the connector body to at least one of the ports disposed on the longitudinal surface of the connector body. The multi-contact connector also includes a flexible-circuit sleeve with a substantially-tubular shape and an exterior surface. The flexible-circuit sleeve includes a plurality of contact terminals disposed on the exterior surface and at least one slot extending through the flexible-circuit sleeve to allow contact with at least one of the contact terminals from inside the flexible-circuit sleeve. The flexible-circuit sleeve is configured and arranged to be disposed over at least a portion of the connector body.

Another embodiment is a lead assembly that includes a lead. The lead has a proximal end and a distal end. The lead also includes a plurality of electrodes, disposed on the distal end, and a plurality of conductor wires extending along the lead from the distal end to the proximal end. The distal end of at least one of the conductor wires is electrically coupled to at least one of the electrodes. The lead also includes a multi-contact connector electrically coupled to the proximal end of one or more of the conductor wires. The multi-contact connector includes a connector body having a substantially-tubular shape with a longitudinal surface and a distal end. The connector body includes at least one lumen and defines at least one port. At least one of the lumens extends from the distal end of the connector body to at least one of the ports disposed on the longitudinal surface of the connector body. The multi-contact connector also includes a flexible-circuit sleeve with a substantially-tubular shape and an exterior surface. The flexible-circuit sleeve includes a plurality of contact terminals disposed on the exterior surface and at least one slot extending through the flexible-circuit sleeve to allow contact with at least one of the contact terminals from inside the flex-circuit sleeve. The flexible-circuit sleeve is configured and arranged to be disposed over at least a portion of the connector body.

Yet another embodiment is a method for assembling a proximal end of a lead assembly. The method includes disposing a flexible-circuit sleeve over a portion of a longitudinal surface of a connector body. The flexible-circuit sleeve includes a plurality of contact terminals aligned with at least one port extending through the connector body. At least one conductive element is disposed in at least one lumen defined by the connector body. The lumen extends from at least one of the ports to a distal end of the connector body. The proximal end of each of the conductive elements is electrically coupled to at least one of the contact terminals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that include a lead assembly with a multi-contact connector at a proximal end of the lead assembly, as well as methods of making and using the lead assemblies.

Suitable implantable electrical stimulation systems include, but are not limited to, an electrode lead with one or more electrodes disposed on a distal end of the lead and one or more terminals disposed on a proximal end of the lead. Electrodes leads include, for example, percutaneous leads, paddle leads, and cuff leads. Examples of electrical stimulation systems with electrode leads are found in, for example, U.S. Pat. Nos. 6,181,969; 6,516,227; 6,609,029; 6,609,032; and 6,741,892; and U.S. patent application Ser. Nos. 11/238,240; 11/319,291; 11/327,880; 11/375,638; 11/393,991; 11/396,309; 11/532,844; 11/609,586; 11/694,769; 11/773,867; and 11/855,033, all of which are incorporated by reference.

Figure 1:
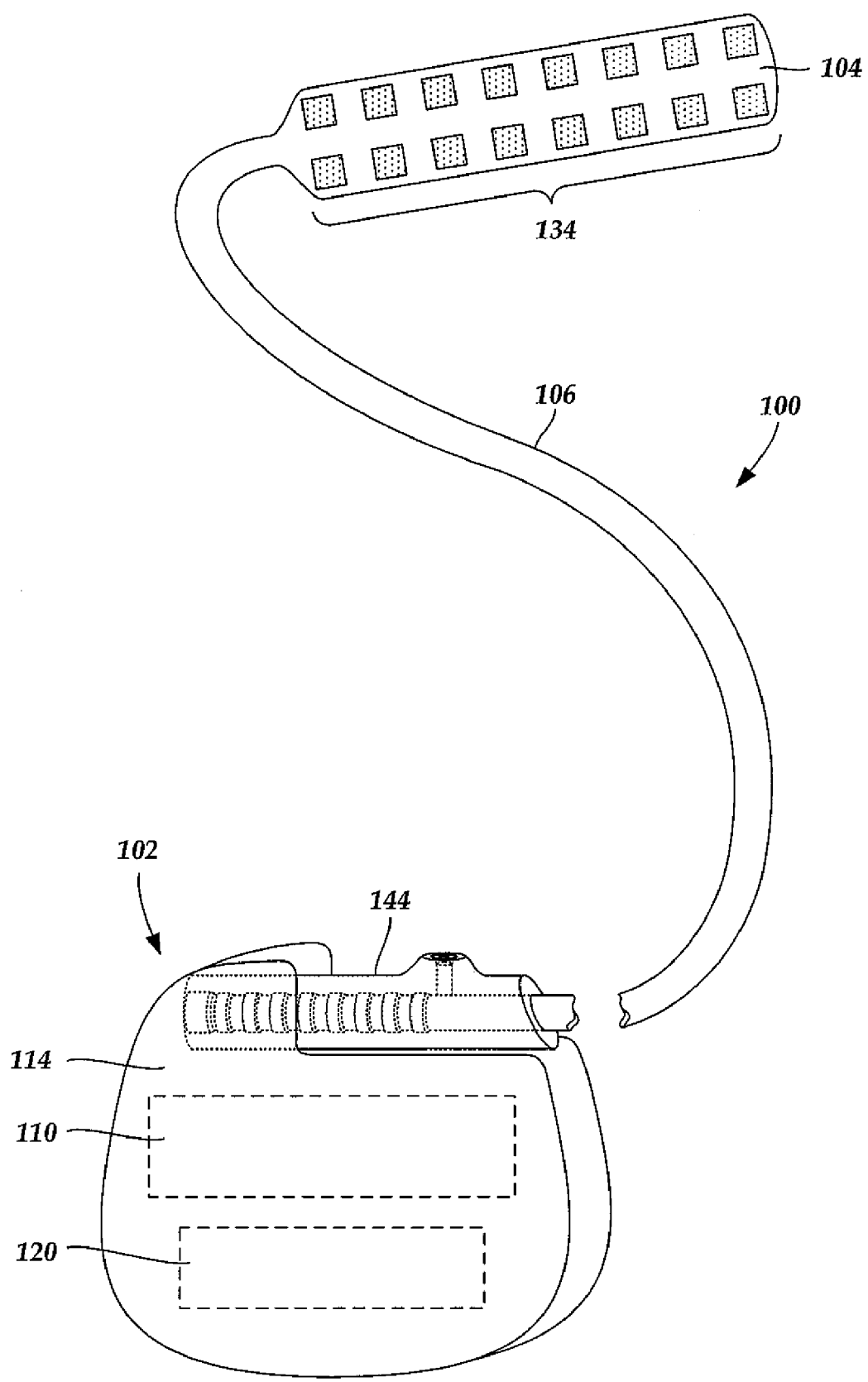
FIG. 1 is a schematic view of one embodiment of an electrical stimulation system, according to the invention.
Figure 2:
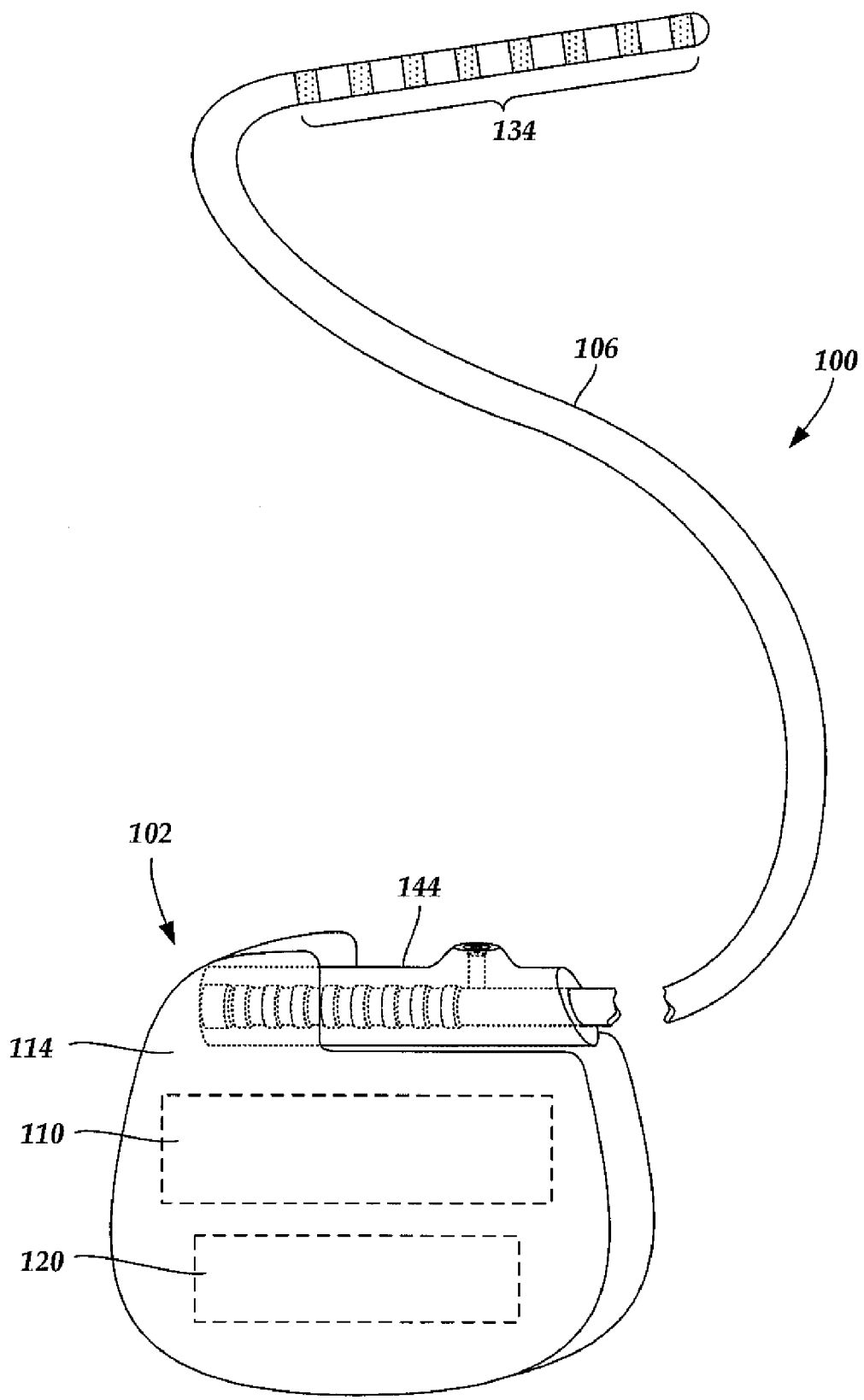
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the lead body 106 form a lead. The paddle body 104 typically includes an array of electrodes 134. The control module 102 typically includes an electronic subassembly 110 and optional power source 120 disposed in a sealed housing 114. The control module 102 typically includes a connector 144 (see FIGS. 2 and 3) into which the proximal end of the lead body 106 can be plugged to make an electrical connection via conductive contacts on the control module 102 and on the lead body 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions (not shown) can be disposed between the lead and the control module 102 to extend the distance between the control module 102 and the lead body 106 of the embodiments shown in FIGS. 1 and 2.

The electrical stimulation system or components of the electrical stimulation system, including one or more of the lead body 106, the paddle body 104 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or lead body 106 are typically disposed in, or separated by, a non-conductive, biocompatible material including, for example, silicone, polyurethane, polyetheretherketone ("PEEK"), epoxy, and the like or combinations thereof. The paddle body 104 and lead body 106 may be formed in the desired shape by any process including, for example, molding (including injection molding), casting, and the like. The non-conductive material typically extends from the distal end of the lead to the proximal end. The non-conductive, biocompatible material of the paddle body 104 and the lead body 106 may be the same or different. The paddle body 104 and lead body 106 may be a unitary structure or can be formed as two separate structures that are permanently or detachably coupled together.

Conductive contacts (see FIGS. 3 and 4A) are typically disposed at the proximal end of the lead for connection to a corresponding conductive contact (not shown in FIG. 1) in the control module 102 (or to conductive contacts on a lead extension). Conductor wires (see FIG. 4A) extend from the conductive contacts to the electrodes 134. Typically, one or more electrodes 134 are electrically connected to a conductive contact. In some embodiments, each conductive contact is only connected to one electrode 134. The conductor wires may be embedded in the non-conductive material of the lead or can be disposed in one or more lumens (see FIG. 4A) extending along the lead. In some embodiments, there is an individual lumen for each conductor wire. In other embodiments, two or more conductor wires may extend through a lumen. There may also be one or more lumens that open at, or near, the proximal end of the lead, for example, for inserting a stylet rod to facilitate placement of the lead within the body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3:
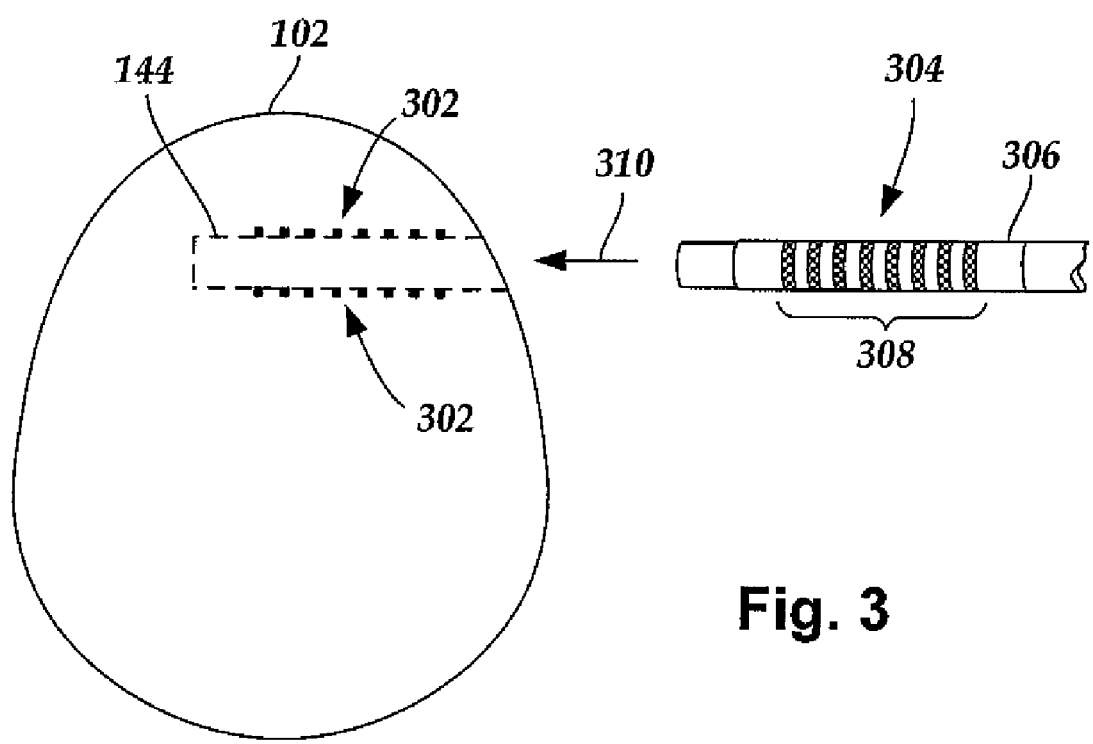
FIG. 3 is a schematic close-up view of a proximal portion of one embodiment of an insertable lead and a control module for an electrical stimulation system, according to the invention.

FIG. 3 is a schematic close-up view of a proximal portion of one embodiment of an insertable lead and a control module for an electrical stimulation system, according to the invention. In FIG. 3, the control module 102 includes a connector 144 with conductive contacts 302 into which a proximal end 304 of a lead 306 with contact terminals 308 can be inserted, as shown by directional arrow 310, to electrically couple the control module 102 to a plurality of electrodes (134 in FIG. 1) at a distal end of the lead 306. Examples of connectors in control modules are found in, for example, U.S. Pat. No.

7,244,150 and U.S. patent application Ser. No. 11/532,844, which are incorporated by reference.

Figure 4A:
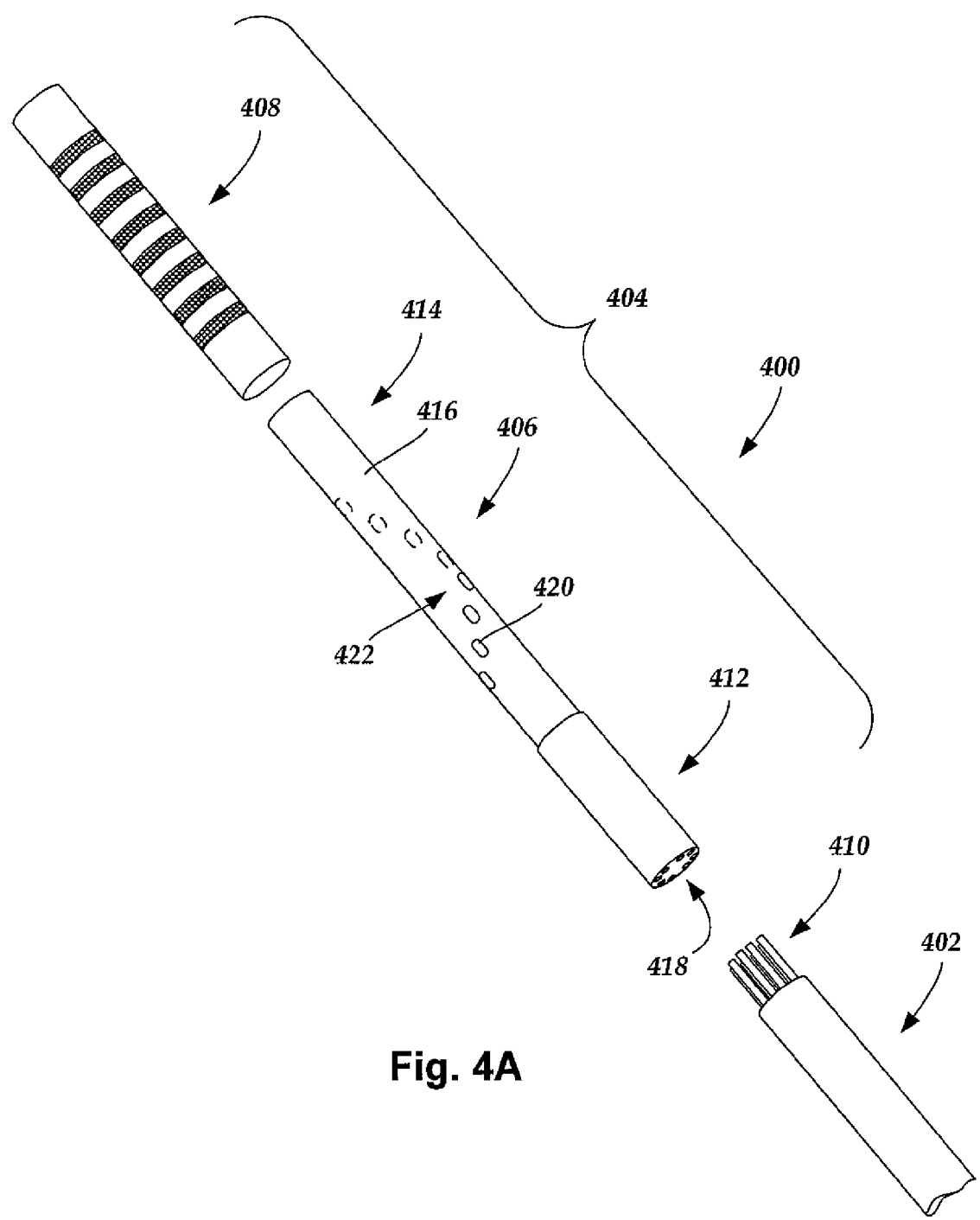
FIG. 4A is a schematic exploded perspective view of one embodiment of a lead assembly for an electrical stimulation system, according to the invention.

FIG. 4A is a schematic exploded perspective view of one embodiment of a lead assembly for an electrical stimulation system. A lead assembly 400 includes a lead 402 (a proximal end is shown) and a multi-contact connector 404. The multi-contact connector 404 includes a connector body 406 and a flexible-circuit sleeve 408. The lead 402 is substantially tubular-shaped and includes conductor wires 410 emerging from the proximal end of the lead 402. The number of connector wires 410 in a lead 402 may vary. For example, there can be one, two, three, four, six, eight, ten, twelve, fourteen, sixteen, or more conductor wires 410. As will be recognized, other numbers of conductor wires 410 may also be used. In at least some embodiments, the number of conductor wires corresponds to the number of electrodes at a distal end of the lead. In other embodiments, more than one electrode is coupled to a conductor wire.

The connector body 406 is substantially tubular-shaped and includes a distal end 412, a proximal end 414, and a longitudinal surface 416. Lumens 418 extend from the distal end 412 of the connector body 406. In at least some embodiments, the number of lumens corresponds to the number of conductor wires. It will be recognized, however, that the number of lumens may be more or fewer than the number of conductor wires. The lumens typically extend to one or more ports, such as port 420. The ports can be disposed in any regular or irregular arrangement. For example, the ports can be disposed in one or more staggered groupings 422 arranged around the circumference of the longitudinal surface 416. The lumens 418 are configured and arranged to allow connection of one or more conductor wires 410 from the lead 402. In one embodiment, additional lumens are incorporated into a lead assembly for additional functions, such as receiving an insertion rod of a stylet used during placement of the lead assembly 400 or for infusion of drugs or medications. The number of ports in a connector body 406 may also vary. For example, there can be one, two, three, four, six, eight, ten, twelve, fourteen, sixteen, or more ports. As will be recognized, other numbers of ports may also be used. In some embodiments, the number of ports corresponds to the number of lumen in a connector body.

Figure 4B:
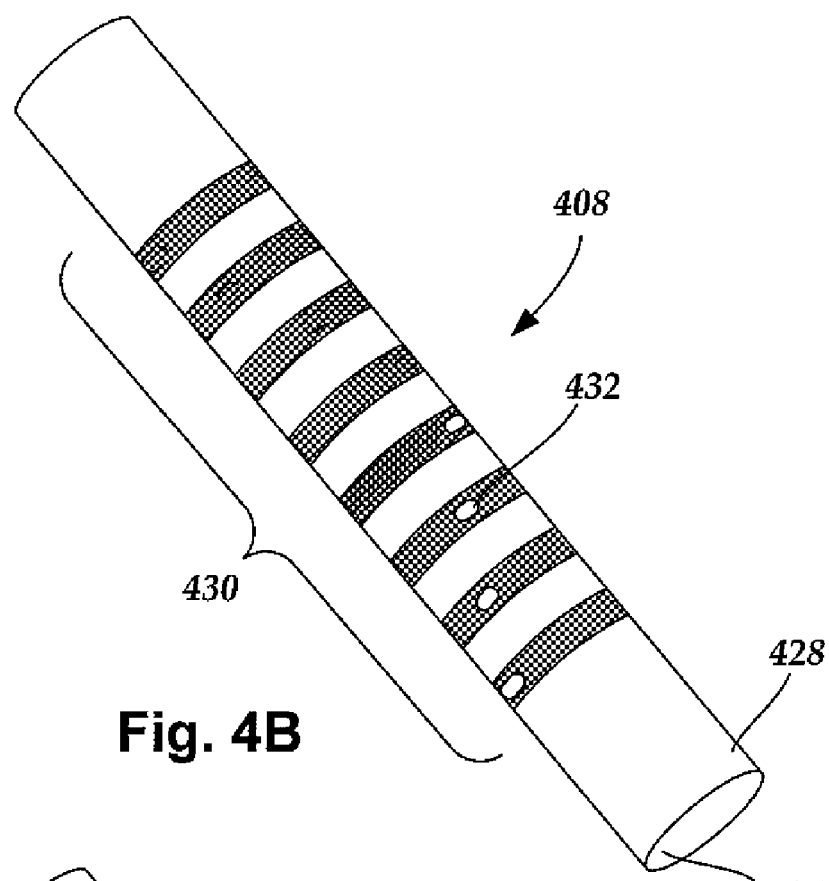
FIG. 4B is a schematic perspective view of one embodiment of a flexible-circuit sleeve for an electrical stimulation system, according to the invention.

FIG. 4B is a schematic perspective view of one embodiment of a flexible-circuit sleeve for an electrical stimulation system. The flexible-circuit sleeve 408 is substantially tubular-shaped and includes an interior surface 426 and an exterior surface 428. Contact terminals 430 are disposed on the exterior surface 428 of the flexible-circuit sleeve 408. The contact terminal can be disposed in a variety of different shapes, such as a strip. In FIG. 4B, the contact terminals are shown as being ring-shaped. In at least some embodiments, the number of contact terminals corresponds to the number of ports. The contact terminals can be disposed in any regular or irregular arrangement. For example, the contact terminals can be disposed around the circumference of the exterior surface 428. In one embodiment, the contact terminals 430 have a width that is between one-half millimeter and two millimeters and are longitudinally spaced apart in regular intervals of between one millimeter and five millimeters. In a preferred embodiment, the longitudinal spacing between adjacent contact terminals 430 corresponds to the longitudinal spacing between adjacent ports disposed on the connector body 406.

Each contact terminal 430 includes a slot, such as slot 432, extending through the flexible-circuit sleeve 408 from each of the contact terminals 430 to the interior surface 426 of the flexible-circuit sleeve 408. In at least some embodiments, the number of slots corresponds to the number of ports. In a preferred embodiment, the placement of the slots corresponds to the placement of the ports disposed on the connector body 406.

Figure 4C:
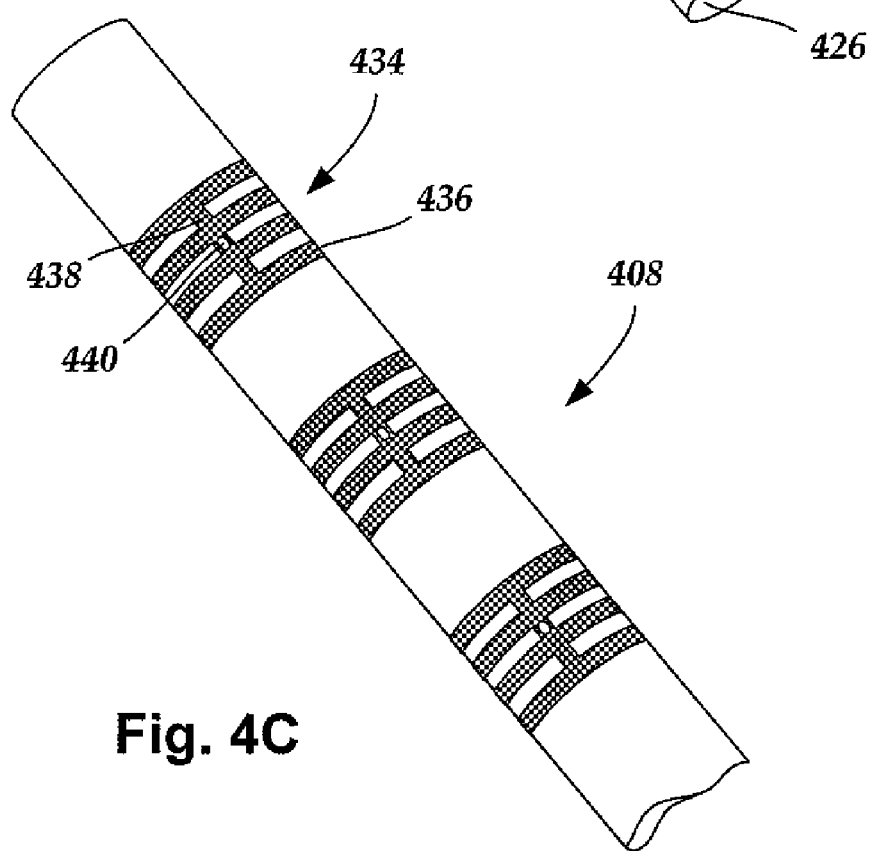
FIG. 4C is a schematic perspective view of another embodiment of a flexible-circuit sleeve for an electrical stimulation system, according to the invention.

FIG. 4C is a schematic perspective view of another embodiment of a flexible-circuit sleeve for an electrical stimulation system. In FIG. 4C, contact terminals, such as contact terminal 434, are disposed on flexible-circuit sleeve 408. Each contact terminal includes a plurality of ring-shaped contact strips, such as contact strip 436, interconnected by one or more contact-strip connectors, such as contact-strip connector 438, and slot 440. The number of contact strips on a contact terminal may vary. For example, there can be one, two, three, four, six, eight, ten, twelve, fourteen, sixteen, or more contact strips. As will be recognized, other numbers of contact strips may also be used. The slot 440 can be disposed in either one of the contact strips or one of the contact-strip connectors. In FIG. 4C, the slot 440 is shown on the contact-strip connector 438. In a preferred embodiment, the placement of the slots corresponds to the placement of the ports disposed on the connector body 406.

Figure 4D:
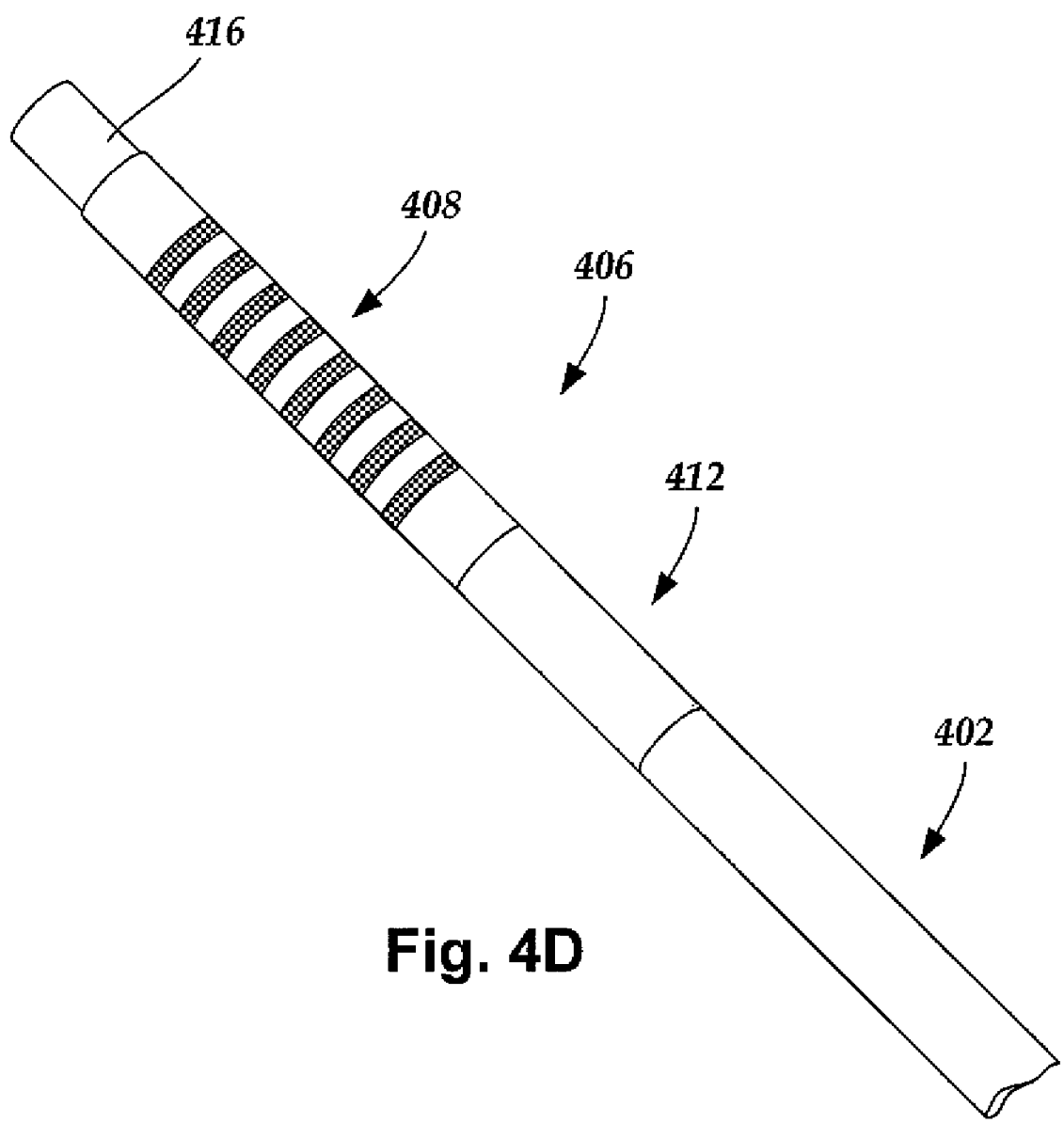
FIG. 4D is a schematic perspective view of one embodiment of an assembled lead assembly for an electrical stimulation system, according to the invention.

FIG. 4D is a schematic perspective view of one embodiment of an assembled lead assembly for an electrical stimulation system. The proximal end of the lead 402 is coupled to the distal end 412 of the connector body 406. Additionally, the flexible-circuit sleeve 408 is inserted over a portion of the longitudinal surface 416 of the connector body 406. When the flexible-circuit sleeve 408 is inserted over a portion of the connector body 406, one or more of the ports can be aligned with one or more slots on one or more contact terminals. Accordingly, in at least some embodiments, one or more conductor wires (see in FIG. 4A) emerging from the lead 402 can be disposed in a lumen (see in FIG. 4A) on the distal end 412 of the connector body 406 and extend out a port (see FIG. 4A), and through a slot (see FIG. 4B) defined in a contact terminal (see FIG. 4B).

When a conductor wire extends through a slot on a contact terminal, the conductor wire can be electrically coupled to the contact terminal. In at least some embodiments, a conductor wire is laser welded or soldered to a contact terminal. In other embodiments, the slots include one or more conductors electrically coupled to both the contact terminal on the exterior surface of the flex-circuit sleeve and a conductive pad disposed on the interior surface of the flex-circuit sleeve. In which case, a conductor wire can be electrically coupled to the contact terminal by laser welding or soldering to the conductive pad. The conductive pad and the one or more conductors within the slot can be formed using any conductive materials. Examples of suitable materials include metals, alloys, conductive polymers, conductive carbon, and the like, as well as combinations thereof.

Figure 5:
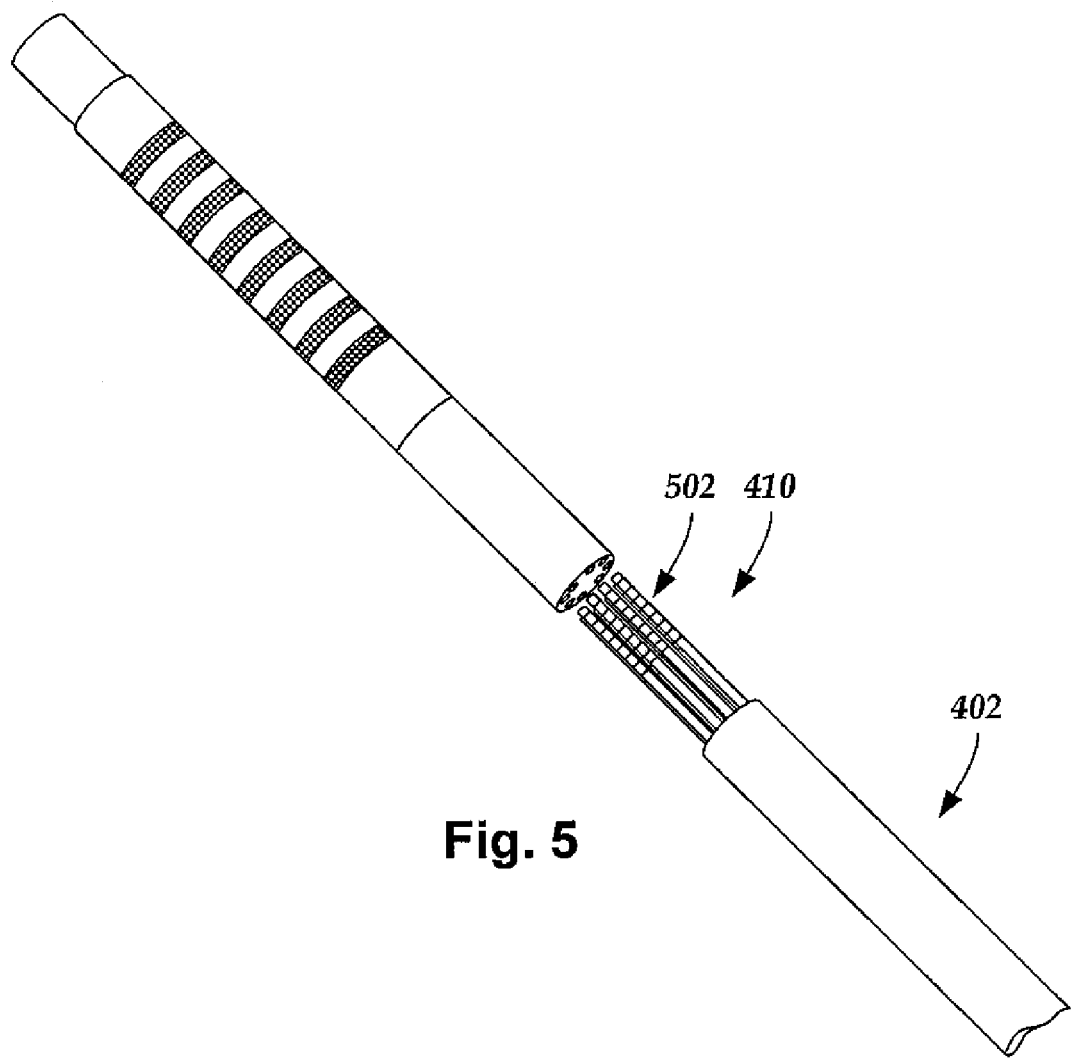
FIG. 5 is a schematic perspective view of one embodiment of a lead assembly illustrating conductor wires from a lead for disposing in lumens of a connector body, according to the invention.
Figure 6:
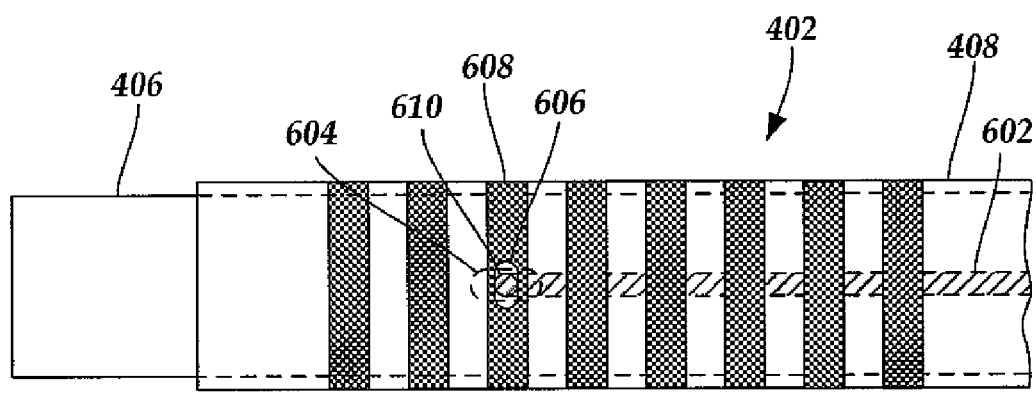
FIG. 6 is a schematic top view of a portion of one embodiment of a lead assembly illustrating a conductor wire electrically coupled to a contact terminal of a multi-contact connector, according to the invention.

FIG. 5 is a schematic perspective view of one embodiment of a lead assembly illustrating conductor wires from a lead for disposing in lumens of a connector body. In FIG. 5, the conductor wires 410 are shown extended from the proximal end of the lead 402. The conductor wires 410 include proximal ends 502, shown in FIG. 5 with cross-hatching. FIG. 6 is a schematic top view of a portion of one embodiment of a lead assembly illustrating a conductor wire electrically coupled to a contact terminal of a multi-contact connector. In FIG. 6, the flexible-circuit sleeve 408 of the multi-contact connector 402 is shown inserted over the connector body 406. A conductor wire 602 is disposed in a lumen (see FIG. 4A). The conductor wire 602 extends through a port 604 in the connector body 406, and through a slot 606 in a contact terminal 608. The tip of the proximal end 610 of the conductor wire 602 is electrically coupled to the contact terminal 608. In some embodiments, the conductor wire 602 is disposed in the lumen by inserting the conductor wire through the slot 606, into the port 604, and out the distal end (see FIG. 4A) of the connector body 406. In other embodiments, the conductor wire 602 is disposed in the lumen by inserting the conductor wire 602 into the distal end of the lumen, out the port 604, and through the slot 606.

The flexible-circuit sleeve 408 can be formed using any suitable flexible-circuit substrate material. Examples of suitable substrate materials include polyimide or one or more liquid crystal polymers. In one embodiment, a flexible-circuit sleeve is a continuous cylinder. In another embodiment, a flexible-circuit sleeve includes two or more coupled cylinders. In yet another embodiment, a flexible-circuit sleeve is a split cylinder made by rolling up flat flexible-circuit substrate material.

The contact terminals 430 can be formed using any conductive material suitable for disposition on a flexible-circuit sleeve. Examples of suitable materials include metals, alloys, conductive polymers, conductive carbon, and the like, as well as combinations thereof. In one embodiment, contact terminals 430 are deposited onto the exterior surface 428 of a flexible-circuit sleeve. The contact terminals can be made by any suitable method. The number of contact terminals 430 may vary. For example, there can be two, four, six, eight, ten, twelve, fourteen, sixteen, or more contact terminals 430. In at least some embodiments, the number of contact terminals corresponds to the number of conductor wires of a lead. As will be recognized, other numbers of contact terminals 430 may also be used. In various embodiments, the sizes and numbers of contact terminals 430, as well as the longitudinal spacing between adjacent contact terminals 430, are designed for insertion into a connector 144 of a control module 102 (or a lead extension).

A connector body 406 can be formed using suitable ceramic or plastic material using any suitable manufacturing technique, including molding, extruding, machining, casting, and other types of manufacturing techniques. In at least some embodiments, once the conductor wires 410 disposed in a connector body 406 are electrically coupled to the contact terminals 430 on a flexible-circuit sleeve 408, the flexible-circuit sleeve 408 is permanently attached to the connector body 406. A connector body 406 can be permanently attached to a flex-circuit sleeve using a number of different attachment techniques, including fusing, adhesive-bonding, chemical-bonding, and other attachment techniques. In some embodiments, a connector body 406 is formed from one or more filled or co-extruded high durometer resins, such as a hard polyurethane body with an outer co-extruded layer of polyimide, or other flex-circuit-compatible resin, or one or more liquid crystal polymers.

In at least some embodiments, once the conductor wires 410 are electrically coupled to desired contact terminals 430 and the conductor wires 410 are disposed in a connector body 406 and inserted into a proximal end of a lead 402, the connector body 406 can also be permanently attached to the proximal end of the lead 402 using a number of different attachment techniques, including fusing, adhesive-bonding, chemical-bonding, and other attachment techniques. Accordingly, in embodiments where the connector body 406 is permanently attached to both the flexible-circuit sleeve 408 and the lead 402, the connector body 406 is formed from a material that is permanently attachable to both the flexible-circuit sleeve 408 and the lead 402.

Figure 7:
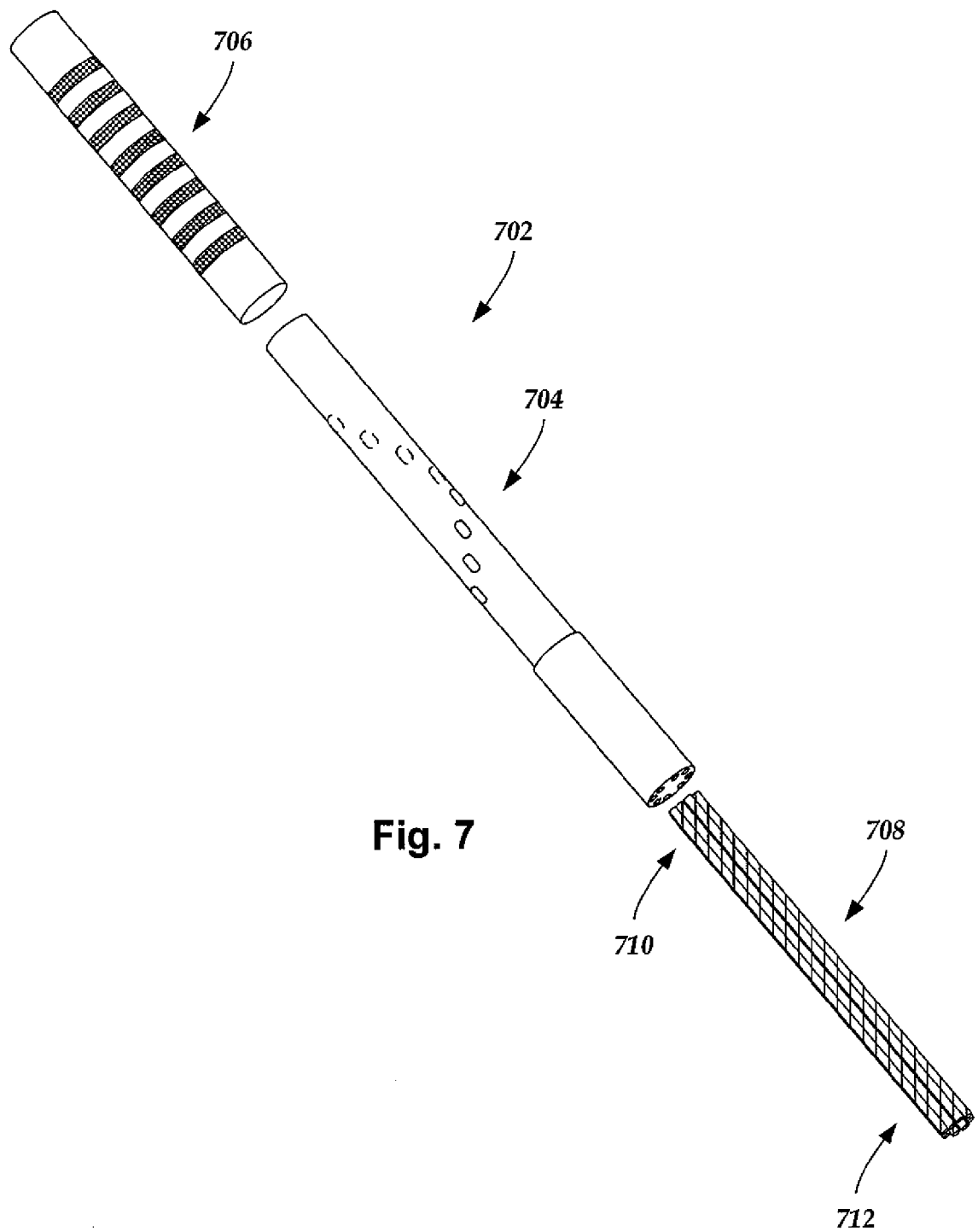
FIG. 7 is a schematic exploded perspective view of a second embodiment of a multi-contact connector for a lead assembly, according to the invention.

FIG. 7 is a schematic exploded perspective view of a second embodiment of a multi-contact connector for a lead assembly, according to the invention. A multi-contact connector 702 includes a connector body 704, a flexible-circuit sleeve 706, and internal connector conductors 708, each internal connector conductor having a proximal end 710 and a distal end 712. In FIG. 7, and in later figures, internal connector conductors are shown with vertical hatching.

Figure 8:
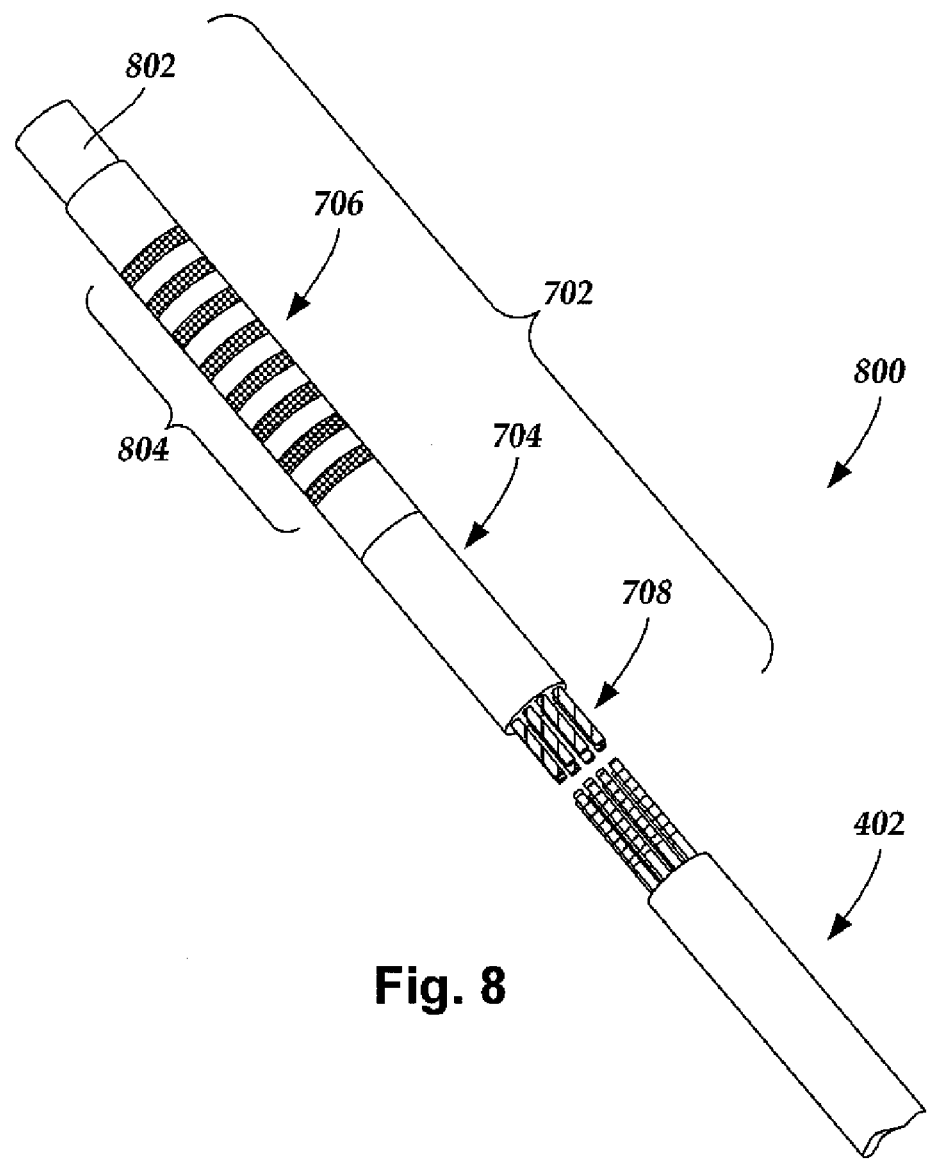
FIG. 8 is a schematic perspective view of a second embodiment of a lead assembly for an electrical stimulation system with the multi-contact connector of FIG. 7, according to the invention.

FIG. 8 is a schematic perspective view of a second embodiment of a lead assembly for an electrical stimulation system with the multi-contact connector 702 of FIG. 7. A lead assembly 800 includes the multi-contact connector 702 and a lead 402. In FIG. 8, the assembled multi-contact connector 702 is configured and arranged for coupling to the lead 402. The flexible-circuit sleeve 706 is inserted over a longitudinal surface 802 of the connector body 704 and slots (see FIG. 4B) extending through the flexible-circuit sleeve 706 are aligned with ports (see FIG. 4A) on the longitudinal surface 802 of the connector body 704. Additionally, the internal connector conductors 708 are disposed in one or more lumens in the connector body 704 and the proximal ends 710 (see FIG. 7) of the internal connector conductors 708 are electrically coupled to one or more contact terminals 804. In at least some embodiments, internal connector conductors 708 are laser welded or soldered to contact terminals 804. In other embodiments, the slots include a conductor electrically coupled to both the contact terminal on the exterior surface of the flex-circuit sleeve and a conductive pad disposed on the interior surface of the flex-circuit sleeve. In which case, a conductor wire can be electrically coupled to the contact terminal by laser welding or soldering to the conductive pad. In at least some embodiments, once the internal connector conductors 708 are electrically coupled to one or more contact terminals, the flexible-circuit sleeve 706 is permanently attached to the connector body 704.

Figure 9:
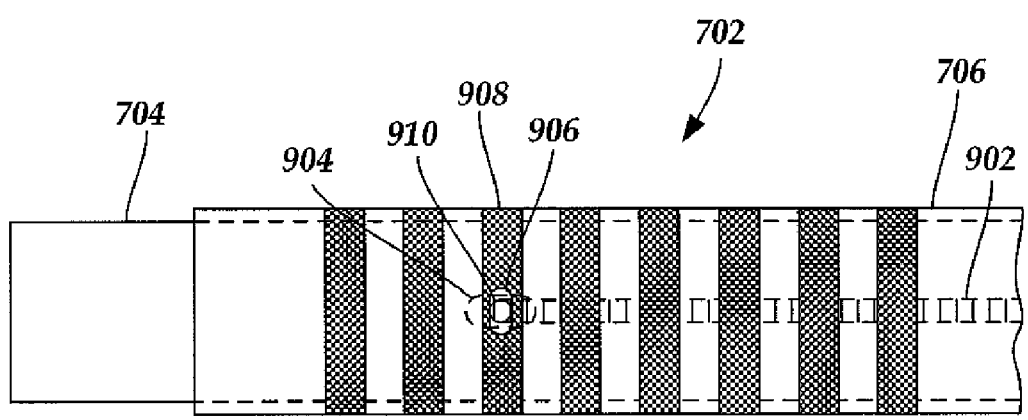
FIG. 9 is a schematic top view of a portion of one embodiment of a lead assembly illustrating an internal connector conductor electrically coupled to a contact terminal of a multi-contact connector, according to the invention.

FIG. 9 is a schematic top view of a portion of one embodiment of a lead assembly illustrating an internal connector conductor electrically coupled to a contact terminal of a multi-contact connector. In FIG. 9, the flexible-circuit sleeve 706 of the multi-contact connector 702 is shown inserted over a portion of the connector body 704. An internal connector conductor 902 is disposed in a lumen (see FIG. 4A). The internal connector conductor 902 extends through a port 904 in the connector body 704, and through a slot 906 in a contact terminal 908. The tip of the proximal end 710 of the internal connector conductor 902 is electrically coupled to the contact terminal 908.

Assembly of a proximal end of a lead may involve a complex and expensive series of assembly steps that need to be performed. One advantage of at least some of the embodiments described above may be simplification of the manufacturing process which, in turn, may result in reduced cost or increased production. Additionally, the multi-contact connector described above, with reference to FIGS. 7-9, may be manufactured separately from leads and subsequently attached. Thus, it may be possible to outsource manufacturing of multi-contact connectors.

Figure 10:
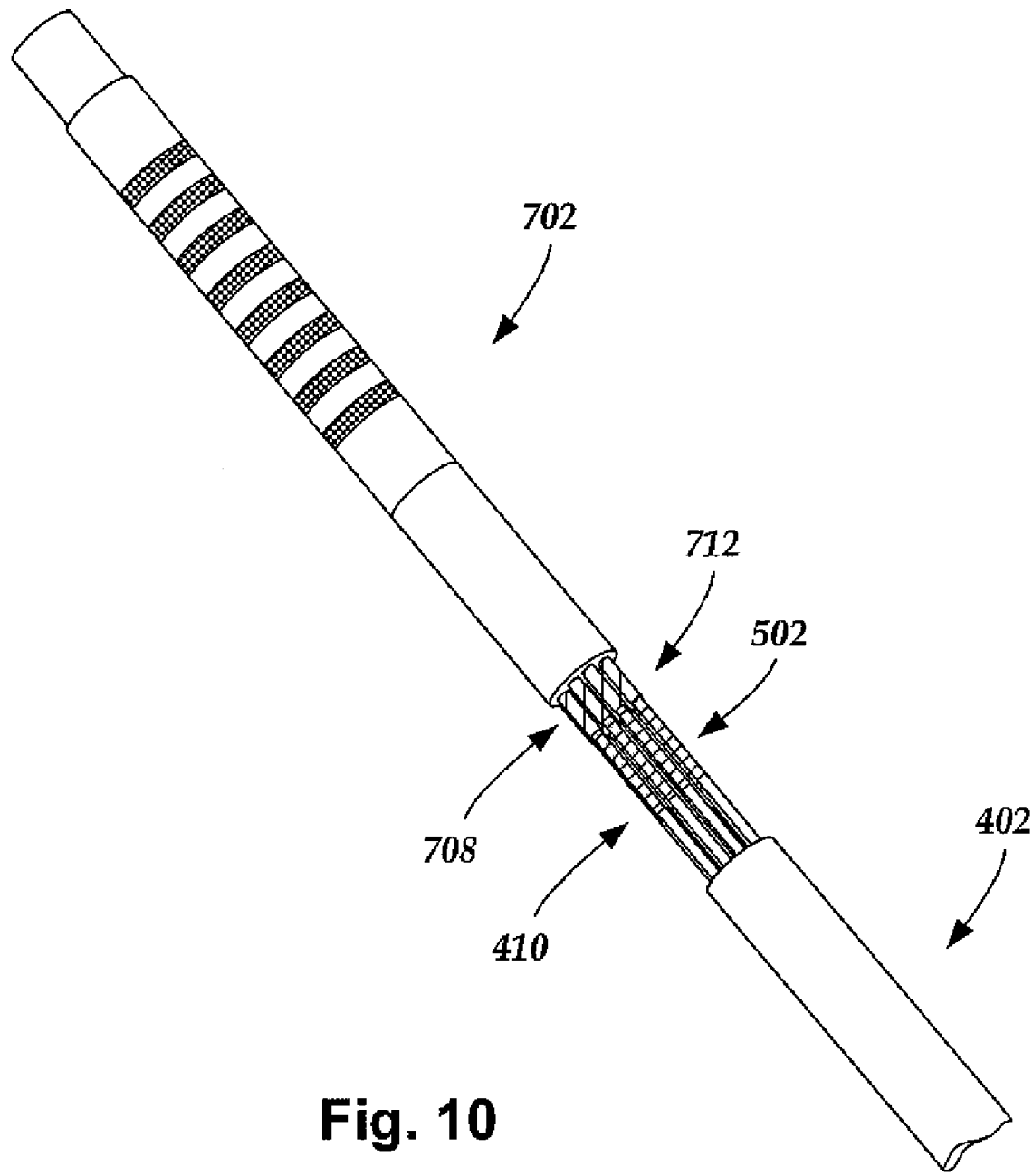
FIG. 10 is a schematic perspective view of one embodiment of a multi-contact connector electrically coupled to a lead and forming a lead assembly, according to the invention.

Once a multi-contact connector is formed, according to the embodiments described above, with reference to FIGS. 7-9, the multi-contact connector may be coupled to a proximal end of a lead to form a lead assembly. FIG. 10 is a schematic perspective view of one embodiment of a multi-contact connector electrically coupled to a lead and forming a lead assembly, according to the invention. In FIG. 10, the distal ends 712 of the internal connector conductors 708 are electrically coupled to the proximal ends 502 of conductor wires 410 emerging from the proximal end of the lead 402. In some embodiments, the tip of the proximal end 502 of one or more conductor wires 410 are disposed in the tip of the distal end 712 of one or more of the internal connector conductors 708. In other embodiments, the tip of the distal end 712 of one or more of the internal connector conductors 708 are disposed in the tip of the proximal end 502 of one or more conductor wires 410. In some embodiments, the conductor wires 410 are laser welded or soldered to the internal connector conductors 708.

Thus, the multi-contact connector 702 can be coupled to the proximal end of the lead 402 via an electric coupling between internal connector conductors 708 and conductor wires 410. Additionally, once the conductor wires 410 are electrically coupled to the internal connector conductors 708, the multi-contact connector 702 can be permanently attached to the proximal end of the lead 402, as shown in FIG. 4C.

Figure 11:
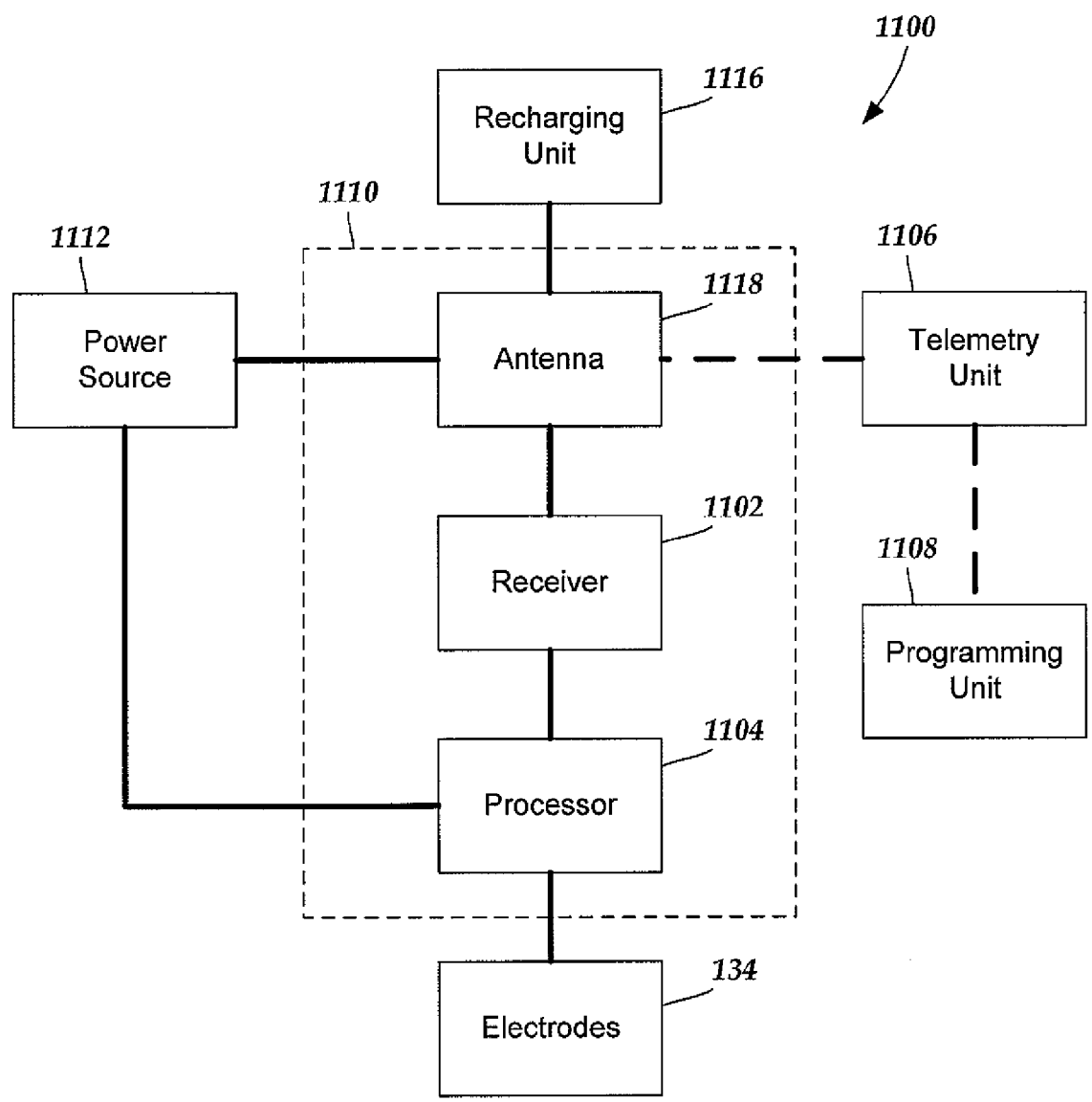
FIG. 11 is a schematic block diagram of components in one embodiment of an electrical stimulation system, according to the invention.

FIG. 11 is a schematic block diagram of components in one embodiment of an electrical stimulation system, according to the invention. An electrical stimulation system 1100 includes an electronic subassembly 1110 disposed within a control module. It will be understood that the stimulation system can include more, fewer, or different components and can have a variety of different configurations including those configurations disclosed in the stimulator references cited herein.

Some of the components (for example, power source 1112, antenna 1118, receiver 1102, and processor 1104) of the stimulation system can be positioned on one or more circuit boards or similar carriers within a housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the stimulation system. A processor 1104 is generally included to control the timing and electrical characteristics of the stimulation system. For example, the processor can, if desired, control one or more of the timing, frequency, strength, duration, and waveform of the pulses. In addition, the processor 1104 can select which electrodes can be used to provide stimulation, if desired. In some embodiments, the processor may select which electrode(s) are cathodes and which electrode(s) are anodes. In some embodiments, the processor may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 208 that, for example, allow modification of pulse characteristics. In the illustrated embodiment, the processor 1104 is coupled to a receiver 1102 which, in turn, is coupled to the optional antenna 1118. This allows the processor to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 1108 can be any unit that can provide information to the telemetry unit for transmission to the stimulation system. The programming unit 1108 can be part of the telemetry unit 1106 or can provide signals or information to the telemetry unit via a wireless or wired connection. One example of a suitable programming unit is a computer operated by the user or clinician to send signals to the telemetry unit.

The signals sent to the processor 1104 via the antenna 1118 and receiver 1102 can be used to modify or otherwise direct the operation of the stimulation system. For example, the signals may be used to modify the pulses of the stimulation system such as modifying one or more of pulse duration, pulse frequency, pulse waveform, and pulse strength. The signals may also direct the stimulation system to cease operation or to start operation or to start charging the battery. In other embodiments, the stimulation system does not include an antenna 1118 or receiver 1102 and the processor 1104 operates as programmed.

Optionally, the stimulation system may include a transmitter (not shown) coupled to the processor and antenna for transmitting signals back to the telemetry unit 206 or another unit capable of receiving the signals. For example, the stimulation system may transmit signals indicating whether the stimulation system is operating properly or not or indicating when the battery needs to be charged. The processor may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A multi-contact connector comprising:
a connector body having a substantially-tubular shape with a longitudinal surface and a distal end, the connector body defining at least one lumen and at least one port, the at least one lumen extending from the distal end of the connector body to the at least one port disposed on the longitudinal surface of the connector body; and
a flexible-circuit sleeve with a substantially-tubular shape and having an exterior surface, the flexible-circuit sleeve comprising a plurality of contact terminals disposed on the exterior surface and at least one slot extending through the flexible-circuit sleeve to allow contact with at least one of the plurality of contact terminals from inside the flexible-circuit sleeve, wherein the flexible-circuit sleeve is configured and arranged to be disposed over at least a portion of the connector body.

2. The multi-contact connector of claim 1, wherein the flexible-circuit sleeve is disposed over the connector body with at least one of the slots aligned with at least one of the ports.

3. The multi-contact connector of claim 2, further comprising at least one conductive element, the at least one conductive element having a proximal end and a distal end, at least one of the conductive elements disposed in one of the lumens with the proximal end of the conductive element electrically coupled to at least one of the contact terminals.

4. The multi-contact connector of claim 3, wherein at least one of the conductive elements is a conductor wire of a lead.

5. The multi-contact connector of claim 3, wherein at least one of the conductive elements is an internal connector conductor.

6. The multi-contact connector of claim 5, wherein the distal end of at least one of the internal connector conductors is configured and arranged for electrically coupling to at least one conductor wire of a lead.

7. The multi-contact connector of claim 3, wherein the connector body is configured and arranged for permanent attachment to a proximal end of a lead.

8. The multi-contact connector of claim 1, wherein the connector body is configured and arranged for permanent attachment to the flex-circuit sleeve.

9. A lead assembly comprising;
a lead having a proximal end and a distal end, the lead comprising
a plurality of electrodes disposed on the distal end of the lead, and
a plurality of conductor wires extending along the lead from the distal end to the proximal end, the distal end of at least one of the conductor wires electrically coupled to at least one of the electrodes; and
a multi-contact connector electrically coupled to the proximal end of one or more of the conductor wires, the multi-contact connector comprising
a connector body having a substantially-tubular shape with a longitudinal surface and a distal end, the connector body defining at least one lumen and at least one port, the at least one lumen extending from the distal end of the connector body to the at least one port disposed on the longitudinal surface of the connector body; and
a flexible-circuit sleeve with a substantially-tubular shape and having an exterior surface, the flexible-circuit sleeve comprising a plurality of contact terminals disposed on the exterior surface and at least one slot extending through the flexible-circuit sleeve to allow contact with at least one of the plurality of contact terminals from inside the flexible-circuit sleeve, wherein the flexible-circuit sleeve is configured and arranged to be disposed over at least a portion of the connector body.

10. The lead assembly of claim 9, wherein the flexible-circuit sleeve is disposed over the connector body with the at least one slot aligned with the at least one port.

11. The lead assembly of claim 10, wherein at least one of the conductor wires is disposed in one of the lumens of the connector body with the proximal end of the conductor wire attached to at least one of the contact terminals.

12. The lead assembly of claim 10, wherein at least one internal connector conductor is disposed in one of the lumens of the connector body, the at least one internal connector conductor having a proximal end and a distal end, the proximal end electrically coupled to at least one of the contact terminals and the distal end configured and arranged to electrically couple to the proximal end of one of the conductor wires of the lead.

13. The lead assembly of claim 9, wherein the connector body is permanently attached to the proximal end of the lead.

14. The lead assembly of claim 9, wherein the connector body is permanently attached to the flex-circuit sleeve.

15. The lead assembly of claim 9, wherein the multi-contact connector is configured and arranged for insertion into a connector of a control module for an electrical stimulation system.

16. A stimulation system, comprising:
the lead assembly of claim 9; and
a control module coupleable to the lead assembly.

17. A method for assembling a proximal end of a lead assembly, the method comprising:
providing the multi-contact connector of claim disposing the flexible-circuit sleeve of the multi-contact connector over a portion of the longitudinal surface of the connector body of the multi-contact connector;
disposing at least one conductive element in the at least one lumen defined by the connector body; and
electrically coupling a proximal end of the at least one conductive element to at least one of the plurality of contact terminals of the flexible-circuit sleeve.

18. The method of claim 17, wherein at least one of the conductive elements is a conductor wire of a lead.

19. The method of claim 17, wherein the at least one conductive element is an internal connector conductor configured and arranged for electrically coupling to a conductor wire of a lead.

20. The method of claim 17, further comprising permanently attaching the connector body to the proximal end of a lead.

* * * * *